(12) United States Patent
Adamson et al.

(10) Patent No.: US 11,216,943 B2
(45) Date of Patent: Jan. 4, 2022

(54) METHOD FOR PRODUCING A TWO-DIMENSIONAL WHOLE IMAGE

(71) Applicant: SIRONA DENTAL SYSTEMS GMBH, Bensheim (DE)

(72) Inventors: Anders Adamson, Darmstadt (DE); Markus Erbacher, Mannheim (DE); Steffen Hauth, Mainz-Kostheim (DE); Björn Voss, Heidelberg (DE)

(73) Assignee: DENTSPLY SIRONA INC., York, PA (US)

(*) Notice: Subject to any disclaimer, the term of this patent is extended or adjusted under 35 U.S.C. 154(b) by 0 days.

(21) Appl. No.: 16/621,846

(22) PCT Filed: Jun. 20, 2018

(86) PCT No.: PCT/EP2018/066459
§ 371 (c)(1),
(2) Date: Dec. 12, 2019

(87) PCT Pub. No.: WO2018/234396
PCT Pub. Date: Dec. 27, 2018

(65) Prior Publication Data
US 2021/0097680 A1 Apr. 1, 2021

(30) Foreign Application Priority Data
Jun. 20, 2017 (DE) .......................... 102017210222.5

(51) Int. Cl.
*G06T 5/50* (2006.01)
*G06T 7/00* (2017.01)
(Continued)

(52) U.S. Cl.
CPC ............ *G06T 7/0012* (2013.01); *G06T 5/006* (2013.01); *G06T 5/50* (2013.01); *G06T 11/60* (2013.01);
(Continued)

(58) Field of Classification Search
CPC ........... G06T 7/0012; G06T 7/38; G06T 7/30; G06T 5/006; G06T 5/50; G06T 11/60;
(Continued)

(56) References Cited

U.S. PATENT DOCUMENTS 8,811,771 B2 * 8/2014 Shechtman ........... G06T 3/0056
382/293
9,510,757 B2 * 12/2016 Kopelman ............. A61B 6/469
(Continued)

OTHER PUBLICATIONS

Szeliski, R.: Image Alignment and Stitching; Handbook of Mathematical Models in Computer Vision, 2006, S. 273-292. Springer.
(Continued)

*Primary Examiner* — Antonio A Caschera
(74) *Attorney, Agent, or Firm* — Dentsply Sirona Inc.

(57) ABSTRACT

The invention relates to a method for producing a two-dimensional whole image of a recording region captured by means of a plurality of individual images, each having its own viewing direction and its own distance, wherein a spatial orientation of a main image plane of each individual image relative to a main image plane of the respective further individual image is determined on the basis of an overlap of the respectively captured subregions, and at least a plurality of the individual images are combined in accordance with the spatial orientations to form the whole image. The whole image area is the surface of a torus.

14 Claims, 3 Drawing Sheets

(51) Int. Cl.
*G16H 50/50* (2018.01)
*G16H 30/40* (2018.01)
*G06T 5/00* (2006.01)
*G06T 11/60* (2006.01)

(52) U.S. Cl.
CPC ............ *G16H 30/40* (2018.01); *G16H 50/50* (2018.01); *G06T 2207/30036* (2013.01); *G06T 2207/30168* (2013.01); *G06T 2210/41* (2013.01)

(58) Field of Classification Search
CPC . G06T 2207/30036; G06T 2207/30168; G06T 2210/41; G16H 50/50; G16H 30/40
See application file for complete search history.

(56) References Cited

U.S. PATENT DOCUMENTS

| | | | |
|---|---|---|---|
| 2011/0207074 A1* | 8/2011 | Hall-Holt | A61C 13/00 433/29 |
| 2013/0286174 A1 | 10/2013 | Urakabe | |
| 2014/0365140 A1* | 12/2014 | Popilka | A61C 19/04 702/19 |
| 2017/0056136 A1* | 3/2017 | Adamson | A61B 1/00039 |

OTHER PUBLICATIONS

International Search Report; PCT/EP2018/066459; Sep. 17, 2018 (completed); dated Sep. 28, 2018.
International Preliminary Reporton Patentability; PCT/EP2018/066459; Sep. 17, 2018 (completed); dated Sep. 28, 2018.
Written Opinion of the International Searching Authority; PCT/EP2018/066459; Sep. 17, 2018 (completed); dated Sep. 28, 2018.

* cited by examiner

METHOD FOR PRODUCING A TWO-DIMENSIONAL WHOLE IMAGE

TECHNICAL FIELD

The invention relates to a method for producing a two-dimensional whole image of a recording region captured by means of a plurality of individual images, wherein each individual image captures a subregion of the recording region from its own viewing direction and its own distance to the subregion, and at least a plurality of the individual images are combined in accordance with a determined respective spatial orientation to one another to form the whole image.

BACKGROUND OF THE INVENTION

A variety of methods, which make it possible to capture an object or a whole recording region with the aid of a camera, even if the object or the whole recording region is significantly larger than the measurement field of the camera, are known from the state of the art. The methods are based on merging multiple individual images into one whole image.

The common panoramic functions of digital cameras are examples of this. In panorama mode, the multiple produced individual images are typically projected onto a spherical surface in order to merge them into one whole image. This is possible because it can be assumed that the camera is essentially only rotated as the individual images are being taken, but that the position of the three-dimensional camera in relation to the object size or the size of the recording region changes only insignificantly.

The object of the present invention is to further develop the state of the art. The object is in particular to provide an alternative method for producing a whole image from individual images, which, despite a translational movement of the camera relative to the object/recording region, reliably yields whole images with a high recording quality.

Distortions in the two-dimensional whole image should furthermore be reduced as well.

SUMMARY OF THE INVENTION

One subject matter of the invention is a method for producing a two-dimensional whole image of a recording region captured by means of a plurality of individual images, wherein each individual image captures a subregion of the recording region from its own viewing direction and its own distance to the subregion, each individual image includes a plurality of pixels having at least one color value and/or at least one gray value and/or at least one height value, and the respective subregion captured in each individual image overlaps at least one subregion in at least one respective further individual image. A spatial orientation of a main image plane of each individual image relative to a main image plane of the respective further individual image is determined on the basis of the overlap of the respectively captured subregions and at least a plurality of individual images are combined with one another in accordance with the respective determined spatial orientation to form the whole image.

The spatial orientation of the main image plane of each individual image relative to the main image plane of the further individual image is determined by optimizing a quality value, wherein, for a first relative spatial orientation to at least one first pixel in the main image plane of the individual image, a pixel corresponding to the first orientation is determined in the main image plane of the further individual image, a comparison value for the respective color values and/or gray values of the pixel of the individual image and the corresponding pixel of the further image is created, the quality value is created from the at least one comparison value, and the quality value is at least approximated to a specified target value by changing the relative spatial orientation of the main image plane of the individual image to the main image plane of the further individual image.

The individual images are recorded by means of a recording unit, wherein the recording unit can be moved relative to the object or region to be recorded. According to the position of the recording unit relative to the region or object to be recorded when producing an individual image, the individual image captures a subregion from a specific spatial direction, referred to here as the viewing direction, and for a specific distance between the recording unit and the subregion.

It goes without saying that all of the individual images are merged to form the whole image, or the whole image is alternatively created from a selected portion of the produced individual images.

A plane in the three-dimensional space associated with the respective two-dimensional image is respectively designated as the main image plane, e.g. a determined sharpest plane within the individual image or a nominal focal plane corresponding to the nominal focal length of a camera used to capture the individual image.

The relative spatial orientation specifies the position or the orientation of the main image plane of a first individual image in the three-dimensional space relative to a second individual image. A transformation into a common coordinate system, or a projection of the one individual image onto the other individual image or into the main image plane of the other individual image, can be carried out based on the orientation.

In each case, the starting point of the optimization procedure for finding the relative orientation between two individual images is a first relative spatial orientation between the first and the further individual image. For example, an identity of the main image planes of the two individual images to be oriented is assumed as the first orientation.

It goes without saying that the change of the relative spatial orientation during the optimization procedure is not restricted, i.e. it includes six degrees of freedom.

It also goes without saying that, for each relative spatial orientation, all points in the main image plane of the individual image are advantageously determined, to which a pixel corresponding to the relative spatial orientation exists in the main image plane of the further individual image. Furthermore, a comparison value is advantageously calculated for each pair consisting of a pixel of the individual image and the corresponding pixel of the further image, and all calculated comparison values are used as the basis for the quality value.

If the relative spatial orientation assumed in the optimization procedure corresponds to the actual spatial orientation of the main image planes to one another, the pixel and the corresponding pixel respectively depict the same region of the object/region to be captured or have captured said region, and the values of the pixel and the corresponding pixel are the same or differ from one another only slightly.

The progress of the optimization procedure is checked by comparison with the target value. The target value is a limit value to be reached, for example, or differs from a limit value to be reached by a specified value.

One advantage of the method according to the invention is that the orientation between the individual images is determined without further aids, such as markers or structures identified in the images, and without further assumptions/approximations, such as a translationally unchanged camera position. The optimization procedure or the quality value are based solely on the image data itself, i.e. the values of the pixels of the individual images. This makes use of the fact that the pixel values of pixels that capture the same object region are similar or even the same, regardless of whether the pixel values represent color values or gray values.

The at least one pair of pixels is determined by projecting the individual image and the further individual image, or an intermediate image comprising the further individual image, onto a whole image area, wherein the projection is carried out on the basis of the relative spatial orientation and a relative spatial orientation of the individual image or the further individual image to the whole image area. The whole image area is the surface of a torus.

Using the method according to the invention, it is possible to produce a two-dimensional whole image with particularly high resolution. In particular, the resolution of the 2D whole image according to the invention is significantly better than the resolution of a two-dimensional whole image produced by the projection of a three-dimensional whole image produced, for example, by means of an intraoral camera.

Distortions in the two-dimensional whole image are furthermore reduced as well.

Advantageously, the respective individual images are a color image of a camera or a grayscale image of a camera or a three-dimensional image having a texture. Texture typically refers to an image of the surface quality.

At least one pair of pixels consisting of a pixel of the individual image and a corresponding pixel of the further individual image can be determined by projecting the individual image into the main image plane of the further individual image or by projecting the further individual image into the main image plane of the individual image, whereby the projection is carried out according to the relative spatial orientation.

The pixel pair is alternatively determined by projecting the individual image onto an image plane of an intermediate image comprising the further individual image or by projecting an intermediate image comprising the further image onto the main image plane of the individual image.

Using a projection or transformation corresponding to the relative spatial orientation, the images are transformed into a common image plane or onto a common image surface. As a result of the projection or transformation, pixels of the individual image and the further individual image coincide, whereby pixels that coincide or are imaged on top of one another form a respective pair of pixels.

With respect to all of the alternatives mentioned above, projection refers to a projective transformation.

The whole image is formed incrementally by adding the individual image to an intermediate image which at least includes the further individual image, wherein, prior to the addition, the individual image is projected into an image plane of the intermediate image, or, prior to the addition, the intermediate image is projected into the main image plane of the individual image.

Alternatively, a whole image plane is defined and all of the individual images are projected into the whole image plane prior to the addition. The image plane of the intermediate image accordingly lies within or coincides with the whole image plane.

Advantageously, a fixed point in the space is determined for each individual image, wherein a path, which at least includes most of the fixed points, is calculated in the space, individual images belonging to fixed points on the path are selected and the whole image is calculated from the selected individual images.

The path is used to make a selection of individual images that are intended to contribute to the whole image. Individual images recorded from camera positions too far away from the rest of the images, for example, and/or recorded after or during a backward movement of the camera, are discarded.

The fixed point for an individual image advantageously corresponds to a position of a camera when capturing the individual image or to a pixel of the individual image in the main image plane depicted on a sensor center of a recording camera or an image center of the individual image in the main image plane.

The path is advantageously determined on the basis of the distances between two respective fixed points and on the basis of a direction vector between the individual images belonging to the fixed points.

Alternatively, a global registration card is created, i.e. an attempt is made to align every individual image with every other individual image and, if successful, the relative spatial orientation and/or a distance between the individual images is noted in the registration card. Subsequently, using the noted orientations or distances, a shortest path from a first individual image to a last individual image is sought and images outside the path are discarded. Alternatively, the global registration card is used to determine a spanning tree and individual branches are subsequently discarded.

Advantageously, an image center in the main image plane of the individual image is determined for each individual image to be used to form the whole image, whereby the image centers of the individual images are converged by means of a parameterized curve and, prior to merging to form the whole image, each individual image is trimmed along a first and a second cutting edge, whereby the first and the second cutting edge respectively extends inside the main image plane and perpendicular to the curve.

Trimming the individual images makes it in particular possible to avoid unnecessary or even undesired overlapping of the individual images when merging them to form the whole image. Even though overlapping is necessary for determining the relative spatial orientation between two individual images, overlapping can negatively affect the quality of the whole image when the images are merged and is avoided by appropriate trimming of the individual images.

The image center advantageously corresponds to a pixel of the individual image in the main image plane depicted on a sensor center of a recording camera or a geometric centroid of the individual image in the main image plane.

Advantageously, the first cutting edge and the second cutting edge are respectively at a distance to the image center of the individual image, wherein the distance is between 40% and 60% of a distance of the image center to the previous or the next image center on the curve.

According to a first alternative embodiment, the cutting edges are selected such that adjacent individual images abut one another exactly along the cutting edges or the cutting edges of adjacent individual images coincide. In a second alternative embodiment, the cutting edges are selected such that the individual images overlap in a region adjacent to the cutting edge.

Prior to trimming the individual images, at least one image center is advantageously moved along the curve or parallel to the curve within the image plane to a new position. By moving an image center, the cutting edges determined relative to the image center are also moved accordingly. Moving makes it possible to equalize differences in the distances between adjacent image centers along the curve and improve the quality of the whole image.

Advantageously, each first subregion captured in one of the individual images overlaps at least one further subregion captured in one of the further individual images by at least 30% or at least 40% or at least 50% of the first subregion. The greater the overlap, i.e. the proportion of overlap in the respective captured subregion, the more reliably and accurately the relative spatial orientation can be determined.

A subregion of each individual image that is adjacent to the cutting edge is advantageously crossfaded with a subregion of an adjacent individual image. The subregions are preferably linearly crossfaded in a direction perpendicular to the cutting edge.

The individual images are advantageously captured by means of a 2D intraoral camera or a 3D intraoral camera.

BRIEF DESCRIPTION OF THE DRAWINGS

Design examples of the invention are illustrated in the drawing. The figures show.

DETAILED DESCRIPTION OF THE INVENTION

Figure 1:
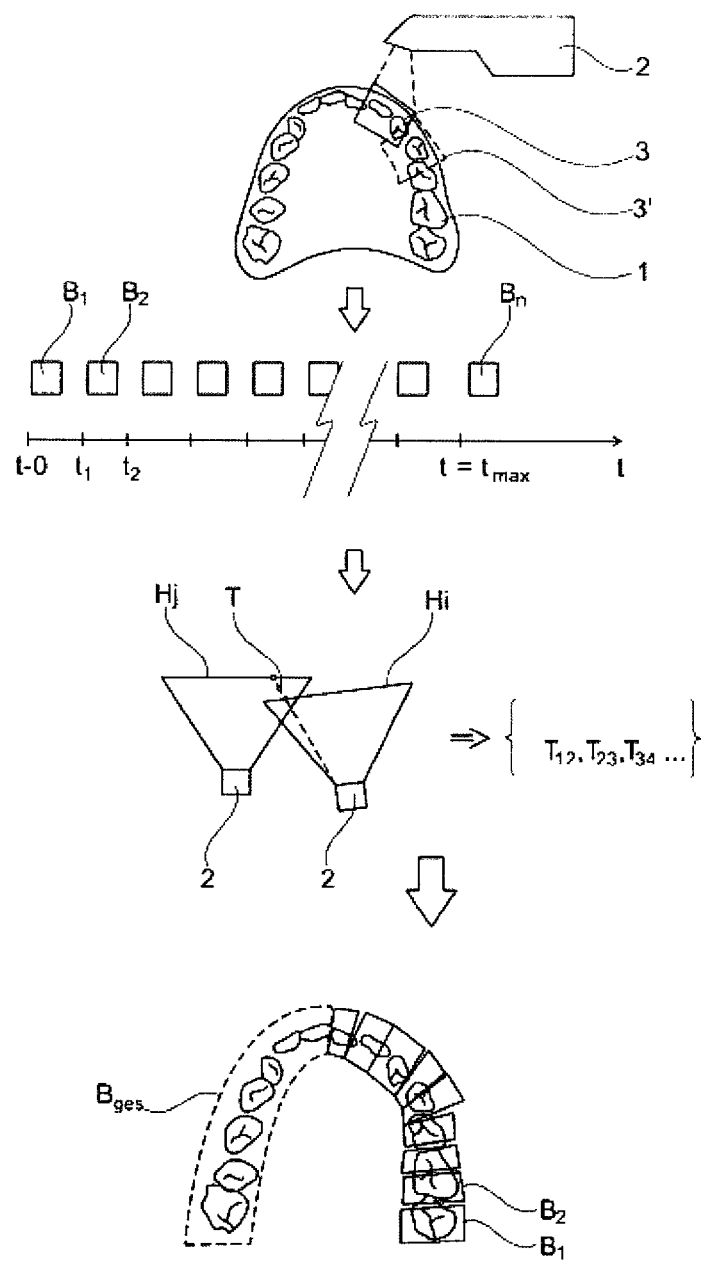
FIG. 1 a procedure according to a first embodiment.

Method steps according to a first embodiment of the method according to the invention are schematically illustrated in FIG. 1.

In this design example, a lower jaw is captured with the aid of an intraoral camera 2 as recording region 1. For this purpose, the camera 2 is moved over the lower jaw 1 during a recording time interval t=0 to t=tmax, in the course of which subregions 3 of the recording region 1 are successively captured in individual images Bi, whereby i=1 . . . N.

Each individual image Bi includes a matrix of n×m pixels, whereby each pixel comprises a gray value. According to alternative embodiments, every pixel has a color value or multiple color values or a height value.

In order to produce a two-dimensional whole image Bges of the recording region 1 on the basis of the multiple individual images Bi, a relative spatial orientation to at least one further individual image Bj is determined for each individual image Bi, whereby the individual image Bi and the further individual image Bj are not identical, but the subregion 3 captured in the individual image Bi at least overlaps a subregion 3' captured in the further individual image Bj. The two individual images Bi and Bj are two temporally successively captured images, for example.

The relative orientation of the two individual images Bi and Bj to one another is determined by means of an optimization procedure. A sharpest plane is assumed as the main image plane Hi and Hj for each of the individual images Bi and Bj; and a first relative spatial orientation of the two main image planes Hi and Hj to one another is assumed.

The first individual image Bi is projected onto the further individual image Bj according to this first spatial orientation. The projection can be carried out in the same way the other way around. The projection is carried out by means of a transformation Tij of the pixels of the first individual image Bi from the main image plane Hi into the main image plane Hj of the further individual image Bj, whereby pixels corresponding at least to a portion of the pixels of the first individual image Bi are determined in the further individual image Bj. A difference of the associated gray values is respectively calculated for each pair of corresponding pixels in the first and the further individual image Bi and Bj, and a quality value is created on the basis of said difference.

Since such pixels in the individual image Bj and the further individual image Bi, which capture the same point of the region or object to be captured, coincide or at least differ only slightly with respect to the captured value, the calculated difference decreases the better the assumed orientation between the main image planes Hi and Hj of the two individual images Bi and Bj coincides with the actual orientation of the single images Bi and Bj. Thus, by minimizing the calculated difference or optimizing the quality value accordingly, the assumed orientation can be approximated to the actual orientation.

The quality value is accordingly optimized by changing the relative spatial orientation of the first and the further individual image Bi and Bj to one another and/or approximated to a specified target value. The target value itself can serve as a termination condition for the optimization procedure.

The starting point of the optimization procedure is a first relative spatial orientation between the first and the further individual image Bi and Bj, e.g. an identity of the two main image planes Hi and Hj, from which the relative spatial orientation is incrementally changed by a relative displacement and/or a relative rotation of the one main image plane Hi or Hj with respect to the other main image plane Hj or Hi. For each changed spatial orientation, the one individual image Bi or Bj is again projected onto the other individual image Bj or Bi and, for pixel pairs of corresponding pixels of the two individual images Bi and Bj, the difference of the gray values is calculated and the quality value is created.

Using the optimization procedure, at least one relative spatial orientation to a further individual image Bj, or to an intermediate image comprising the further individual image Bj, is determined for each individual image Bi.

The whole image Bges is assembled using the determined relative spatial orientations. For example, a first individual image B1 is projected into the main image plane of a second individual image B2, the two individual images B1 and B2 are merged to form a first intermediate image, the first intermediate image is then projected into the main image plane of a third individual image B3, the first intermediate image and the third individual image are merged to form a second intermediate image, and so on.

The first or last individual image captured or an individual image captured at another optimal time, for example, is selected as the first individual image B1. Or an individual image capturing the first or second edge of the recording region 1 or an individual image capturing a central subregion 3 of the recording region 1 is selected as the first individual image. By selecting an individual image that captures a central subregion 3 of the recording region 1, distortions can be reduced or prevented.

Figure 2:
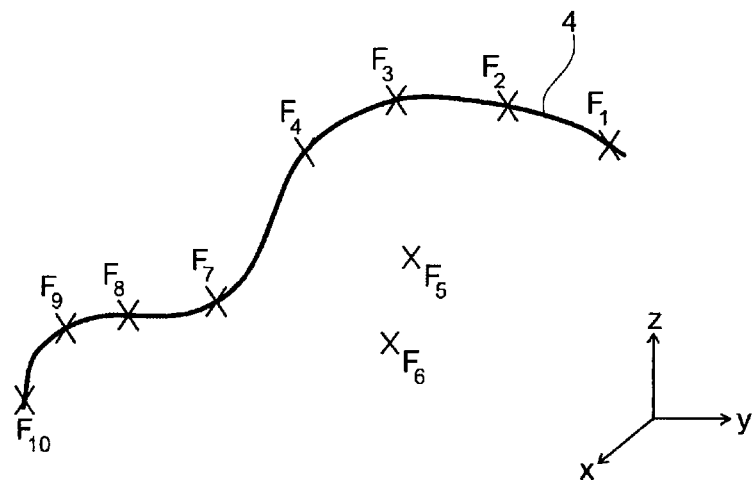
FIG. 2 a path determined on the basis of a design according to the invention.

According to a further development, not all of the individual images are used for the whole image Bges; instead a selection is made, or a portion of the individual images Bi is discarded. For this purpose, a path 4 is calculated as shown schematically in FIG. 2. The fixed points Fi form the starting point for the path, whereby a fixed point Fi is calculated for each individual image Bi. According to a first embodiment, for each individual image Bi, the fixed points Fi respectively represent a three-dimensional camera position from which the individual image Bi was captured. In each case, the camera position is determined on the basis of the individual image Bi and the specific relative spatial orientation of the associated main image plane Hi.

The path 4 is then determined as a connecting line from a first fixed point F1 to a last fixed point FN, and outliers or backward movements with respect to the further fixed points Fi, whereby i=2 . . . N−1, are discarded.

The path 4 is determined using cost functions, for example, whereby a cost function is set up for each connection from a first fixed point Fi to a further fixed point. For example, the cost function takes into account both the distance between the first fixed point Fi and the further fixed point Fj and a direction vector between the main image plane Hi of the first individual image Bi belonging to the first fixed point Fi and the main image plane Hj of the further individual image Bj belonging to the further fixed point Fj. The translational component of a projection of the main image plane Hi of the one individual image Bi onto the main image plane Hj of the further individual image Hj serves as the direction vector, for example.

The path 4 determined on the basis of the cost functions typically traverses most of the fixed points Fi between the first fixed point F1 and the last fixed point FN, whereby strongly deviating or decreasing fixed points Fi are not traversed by the path 4.

The whole image is then composed only of individual images Bi, the fixed points Fi of which are traversed by the path 4. The individual images Bi, the fixed points Fi of which are not traversed by the path 4, are discarded.

According to a further embodiment, the individual images Bi used for the whole image Bges are trimmed prior to merging, i.e. only a portion or section of each individual image Bi is used for the whole image Bges. For this purpose, two cutting edges S1i and S2i are determined for each individual image Bi as shown schematically in FIG. 3. For all of the individual images Bi to be used for the whole image Bges, a reference pixel Pi is determined, e.g. a respective image center. The reference pixels Pi are transformed into a common coordinate system on the basis of the specific relative spatial orientation of the respective main image planes Hi and approximated in the common coordinate system by a curve 5 having a predetermined basic shape, e.g. a parabola or hyperbola or a circle. As outlined in FIG. 3, for example, the procedure is started with a curve 5' having a first parameter set. The distances to the reference pixels Pi are then minimized by changing the parameters of the parameter set. The result of the minimization is the curve 5.

The cutting edges S1i and S2i are determined on the basis of the curve 5 as lines which extend perpendicular to the curve 5. If the reference pixels Pi are always the center point of the respective individual image Bi, the cutting edge S1i or S2i is selected such that it passes through a point on the curve that is equidistant to reference pixels Pi of two adjacent individual images Bi and Bi+1.

Figure 3:
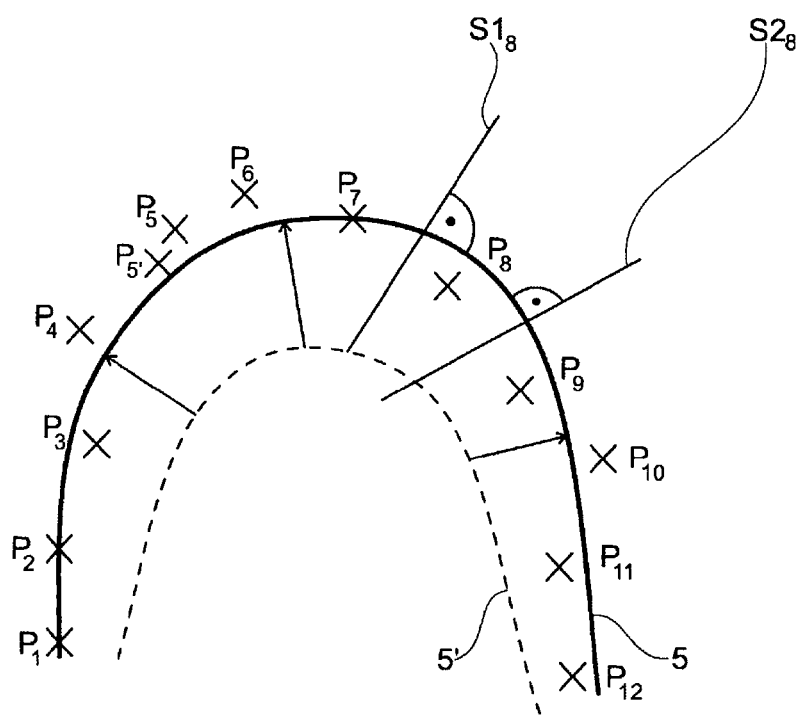
FIG. 3 a determination of cutting edges for individual images according to one further development, FIG. 4A,B a sketch to illustrate the projection according to the invention.

According to a further development, the positions of the reference pixels Pi on the curve 5 or the distances of the reference pixels Pi to one another are checked prior to the determination of the cutting edges S1i and S2i and, if necessary, individual reference pixels Pi are shifted in order to obtain as uniform a distance as possible between all of the successive reference pixels Pi along the curve. FIG. 3 shows an example of this for the reference pixel P5, which is shifted toward the reference pixel P5'. The distance between the reference pixels Pi which are too close to one another is artificially increased by moving at least one of the two reference pixels Pi along the curve 5. The cutting edges S1i and S2i are then calculated taking into account the new position of the reference pixel Pi.

The cutting edges S1i and S2i are selected such that cutting edges of respective adjacent individual images Bi and Bi+1 coincide or adjoin one another. Alternatively, the cutting edges S1i and S2i are selected such that respective adjacent individual images Bi and Bi+1 have an overlap of a specified width, whereby it is advantageous to crossfade the two individual images Bi and Bi+1 in the region of the overlap, in particular linearly, when merging them, i.e. the values of the pixels of the individual images are reduced by an increasing factor in the region of the overlap in the direction perpendicular to the respective cutting edge before the individual images are merged to form the whole image.

Figures 4A, 4B:
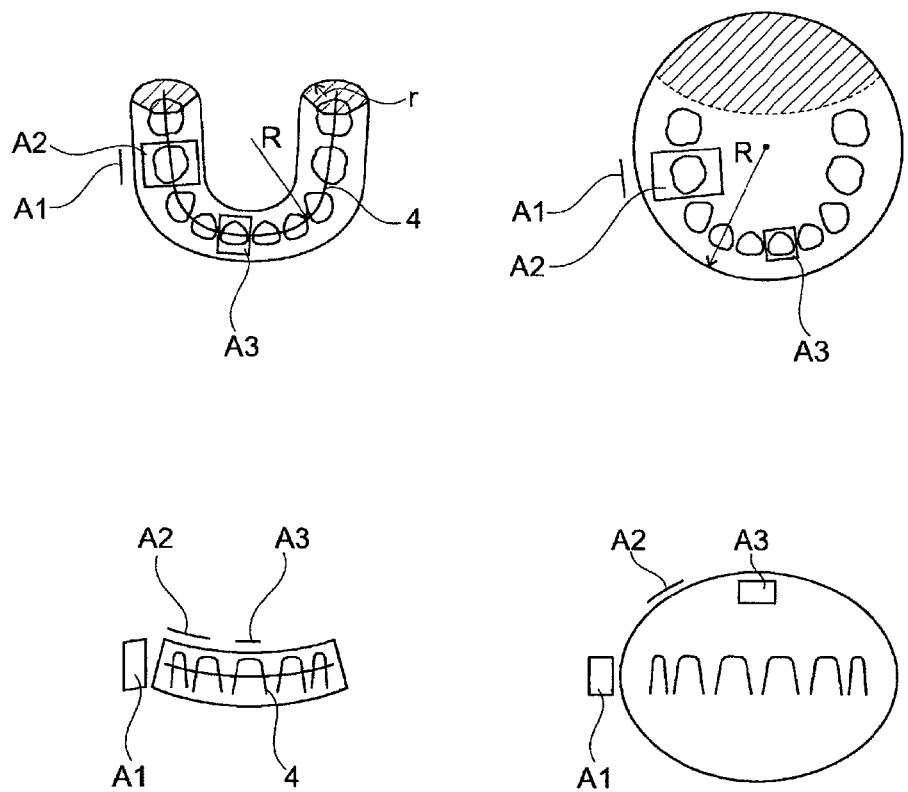

The difference between the projection onto a torus in a 3-dimensional space and the projection onto a sphere is explained with the aid of the sketch of FIGS. 4A and 4B. A torus in the 3-dimensional space is the set of points that have the fixed distance r from a circular curve having the radius R, whereby r<R. A sphere in the 3-dimensional space is the set of points having the fixed distance R from a center point.

The torus can be seen in FIG. 4A, and the sphere can be seen in FIG. 4B; in the upper part in the view from above and in the lower part in the view from the front. Strictly speaking, it is one half of a torus formed by a sectional plane perpendicular to the circular curve having the radius R and a hemisphere.

Three images A1, A2 and A3 are sketched. In image A2 and A3 it can be seen that there are differences in the projection between the sphere and the torus, whereby the images are more distorted with the sphere than with the torus.

The circular curve having the radius R of the torus is determined by the path 4 of the image, so that path 4 is also the skeleton of the torus. The distance r of the torus whereby r<R can likewise be determined from the images or be specified. The torus is thus only completely defined at the end of the recording.

LIST OF REFERENCE SIGNS

1 Recording region
2 Camera
3 Subregion of the recording region
4 Path
5 Curve
5' Curve
A1 Image 1
A2 Image 2
A3 Image 3
Bi Individual image
Bges Two-dimensional whole image
Fi Fixed point
Hi Main image plane
Pi Reference pixel R Radius of the circular curve of the torus or the sphere
r Distance to the circular curve
T Transformation

The invention claimed is:

1. A method for producing a two-dimensional whole image of a recording region captured by means of a plurality of individual images,
   wherein each individual image captures a subregion of the recording region from its own viewing direction and its own distance to the subregion,
   wherein each individual image includes a plurality of pixels having at least one color value or at least one gray value,
   wherein the respective subregion captured in each individual image overlaps at least one subregion in at least one respective further individual image,
   wherein a spatial orientation of a main image plane of each individual image relative to a main image plane of the respective further individual image is determined on the basis of the overlap of the respectively captured subregions and
   wherein at least a plurality of the individual images are combined with one another in accordance with the respective determined spatial orientations to form the two-dimensional whole image,
   wherein the method comprises the steps of:
   determining the spatial orientation of the main image plane of each individual image relative to the main image plane of the further individual image by optimizing a quality value, wherein for a first relative spatial orientation to at least one first pixel in the main image plane of the individual image, a pixel corresponding to the orientation is determined in the main image plane of the further individual image,
   computing a comparison value for the respective color values or gray values of the pixel of the individual image and the corresponding pixel of the further image, by computing a difference of the respective color values or gray values of the pixel of the individual image and the corresponding pixel of the further image
   creating a quality value, responsive to the computing, from the comparison value, wherein the quality value is at least approximated to a specified target value by changing the relative spatial orientation of the main image plane of the individual image to the main image plane of the further individual image, wherein at least one pair of pixels having a pixel of the individual image and a corresponding pixel of the further individual image is determined by projecting the individual image and the further individual image, or an intermediate image having the further individual image, onto a previously determined whole image area, wherein the projection is carried out on the basis of the relative spatial orientation and a relative spatial orientation of the individual image or the further individual image to the whole image area,
   wherein the whole image area is the surface of a torus, and wherein the individual images are captured by means of a 2D intraoral camera or a 3D intraoral camera.

2. The method according to claim 1, wherein the respective individual images are a color image of a camera or a grayscale image of a camera or a three-dimensional image having a texture.

3. The method according to claim 1, wherein the whole image is formed incrementally by adding the individual image to an intermediate image which at least includes the further individual image, wherein, prior to the addition, the individual image is projected into an image plane of the intermediate image, or, prior to the addition, the intermediate image is projected into the main image plane of the individual image.

4. The method according to claim 1, wherein the whole image is formed incrementally by adding the individual image to an intermediate image which at least includes the further individual image, wherein a whole image area is defined and all of the individual images are projected onto the whole image area prior to the addition.

5. The method according to claim 1, wherein
   for each individual image, a fixed point in the space is determined,
   a path which at least includes most of the fixed points is calculated in the space,
   individual images belonging to fixed points on the path are selected and
   the whole image is calculated from the selected individual images.

6. The method according to claim 5, wherein the fixed point for an individual image corresponds to a position of a camera when capturing the individual image or to a pixel of the individual image in the main image plane depicted on a sensor center of a recording camera or an image center of the individual image in the main image plane.

7. The method according to claim 5, wherein the path is determined on the basis of the distances between two respective fixed points and on the basis of a direction vector between the individual images belonging to the fixed points.

8. The method according to claim 1, wherein an image center in the main image plane of the individual image is determined for each individual image to be used to form the whole image, the image centers of the individual images are converged by means of a parameterized curve and, prior to merging to form the whole image, each individual image is trimmed along a first and a second cutting edge, wherein the first and the second cutting edge respectively extends inside the main image plane and perpendicular to the curve.

9. The method according to claim 8, wherein the image center corresponds to a pixel of the individual image in the main image plane depicted on a sensor center of a recording camera or a geometric centroid of the individual image in the main image plane.

10. The method according to claim 8, wherein the first cutting edge and the second cutting edge are respectively at a distance to the image center of the individual image, wherein the distance is between 40% and 60% of a distance of the image center to the previous or the next image center on the curve.

11. The method according to claim 8, wherein, prior to trimming the individual images, at least one image center is moved along the curve or parallel to the curve within the image plane to a new position.

12. The method according to claim 1, wherein each first subregion captured in one of the individual images overlaps at least one further subregion captured in one of the further individual images by at least 30% of the first subregion.

13. The method according to claim 1, wherein a subregion of each individual image adjoining the cutting edge is crossfaded with a subregion of an adjoining individual image.

14. The method according to claim 13, wherein the subregions are linearly crossfaded in a direction perpendicular to the cutting edge.

* * * * *